(12) United States Patent
Matsuura et al.

(10) Patent No.: US 7,029,867 B2
(45) Date of Patent: Apr. 18, 2006

(54) METHOD OF ASSAYING ANTILAMININ-1 ANTIBODY AND APPLICATION THEREOF

(75) Inventors: Eiji Matsuura, 20-801, Nishinocho 7-chome, Okayama-shi (JP); Junko Inagaki, Okayama (JP); Koji Aoki, Nagoya (JP)

(73) Assignee: Eiji Matsuura, Okayama (JP)

( * ) Notice: Subject to any disclaimer, the term of this patent is extended or adjusted under 35 U.S.C. 154(b) by 0 days.

(21) Appl. No.: 10/432,395

(22) PCT Filed: Nov. 20, 2001

(86) PCT No.: PCT/JP01/10138

§ 371 (c)(1),
(2), (4) Date: Sep. 8, 2003

(87) PCT Pub. No.: WO02/42769

PCT Pub. Date: May 30, 2002

(65) Prior Publication Data

US 2004/0082011 A1    Apr. 29, 2004

(30) Foreign Application Priority Data

Nov. 22, 2000 (JP) .............................. 2000-355148

(51) Int. Cl.
  G01N 33/543 (2006.01)
  G01N 33/564 (2006.01)
  G01N 33/536 (2006.01)
  G01N 33/544 (2006.01)
  G01N 33/551 (2006.01)

(52) U.S. Cl. .................. 435/7.95; 435/7.1; 435/7.2; 435/7.21; 435/7.92; 435/7.93; 436/506; 436/518; 436/528; 436/534; 436/536; 436/538; 436/811; 436/906; 600/33

(58) Field of Classification Search .............. 435/7.1, 435/7.2, 7.21, 7.92, 7.93, 7.95, 975; 436/506, 436/518, 528, 534, 536, 538, 811, 906; 530/350, 530/810; 600/33
See application file for complete search history.

(56) References Cited

U.S. PATENT DOCUMENTS 4,340,581 A * 7/1982 Timpl .................. 424/1.57
5,789,260 A * 8/1998 Naparstek ............ 436/506

FOREIGN PATENT DOCUMENTS

JP         4-134097         5/1992

OTHER PUBLICATIONS

Inagaki et al., Apr. 2001. IgG anti-laminin-1 autoantibody and recurrent miscarriages. American Journal of Reproductive Immunology 45: 232-238.*
Foidart et al., 1986. Antibodies to laminin in preeclampsia. Kidney International 29: 1050-1057.*
Bernard et al., 1986. Detection of anti-laminin antibodies in sera by latex agglutination. Clinical Chemistry 32: 1468-1472.*
Chambers et al., 1995. Reproduction and sera embryotoxicity after immunization of monkeys with the laminin peptides YIGSR, RGD, and IKVAV. Proceedings of the National Academy of Sciences USA 92: 6818-6822.*
Qureshi et al., Sep. 2000. Anti-DNA antibodies cross-reacting with laminin i9nhibit trophoblast attachment and migration: implications for recurrent pregnancy loss in SLE patients. American Journal of Reproductive Immunology 44: 136-142.*
Church et al., 1997. Anti-laminin autoantibodies in recurrent miscarriager patients. Placenta 18: A17.*
Yurchenco et al., 1993. Recombinant laminin G domain mediates myoblast adhesion and heparin binding. Journal of Biological Chemistry 268 (11): 8356-8365.*

* cited by examiner

*Primary Examiner*—Long V. Le
*Assistant Examiner*—James L. Grun
(74) *Attorney, Agent, or Firm*—Wenderoth, Lind & Ponack, L.L.P.

(57) ABSTRACT

By allowing serum or plasma samples collected from humans to react with laminin-1 or a fragment thereof, and then determining whether or not anti-laminin-1 antibody, an auto-antibody against laminin-1, in the sample bound to laminin-1 to detect anti-laminin-1 antibody in the sample, gynecology-related diseases such as habitual abortion, sterility, infertility, and endometriosis can be diagnosed.

4 Claims, 3 Drawing Sheets

METHOD OF ASSAYING ANTILAMININ-1 ANTIBODY AND APPLICATION THEREOF

This application is a U.S. national stage of International Application No. PCT/JP01/10138 filed Nov. 20, 2001.

TECHNICAL FIELD

The present invention relates to an assay method for auto-antibody (anti-laminin-1 antibody) against laminin-1, a kit for performing said assay, and uses thereof for clinical applications in the diagnosis of gynecology-related diseases such as habitual abortion, sterility, infertility, and endometriosis.

BACKGROUND ART

Habitual abortion means a condition in which pregnancy is established, but spontaneous abortion and stillbirth are repeated. Causes of habitual abortion are manifold, and abnormal immunological functions are considered to be one of the causes.

As a means to diagnose habitual abortion caused by auto-immunity, there is known a method of determining an auto-antibody, anti-cardiolipin antibody (recently, the antigen of this auto-antibody was demonstrated to be a complex of cardiolipin and β2-glycoprotein I (β2-GPI), and has been designated as β2-GPI-dependent anti-caridiolipin antibody).

However, the above method was not completely reliable, and even a negative result of the assay could not rule out the possibility of habitual abortion. Furthermore, even when the measurement of another marker was combined, satisfactory results could not be obtained. Thus, there has been a need for the development of novel markers different from existing markers.

Also, situations in sterility, infertility, and endometriosis have been similar to those in habitual abortion, and there has been a need for the development of markers that are simpler to determine and are highly reliable.

Laminin is a glycoprotein most abundant in the basement membrane, and is forming a complex with other components of the basement membrane such as nidogen and type IV collagen. Laminin takes the form of an asymmetric cross in which three polypeptides are combined in a coiled form, and the presence of many isoforms has been confirmed. Thus, combinations of three polypeptides, α chain (about 400 kDa), β chain (about 200 kDa) and γ chain (about 200 kDa), that constitute laminin could lead to the formation of various isoforms, and until now the presence of at least 12 isoforms has been reported (J. Cell Biol., 137, 685–701 (1997); J. Cell Biol., 145, 605–618 (1999)).

For example, it has been demonstrated that laminin-1 (α1, β1, γ1) occurs in the kidney, the fetal rain, the retina, blood vessels etc., merosin (=laminin-2; α2, β1, γ1) occurs in the skeletal muscle, the heart, the placenta etc., s-laminin (=laminin-3; α1, β2, γ1) occurs in the basement membrane of the junction of neuromuscular ending plate, endothelium and glomerular basement membrane, s-merosin (=laminin-4; α2, β2, γ1) occurs in Schwann cells, the placenta etc., kalinin/nicein (=laminin-5; α3, β3, γ2) and k-laminin (=laminin-6; α3, β1, γ1) and ks-laminin (=laminin-7; α3, β2, γ1) are peculiar to the basement membrane of the skin.

The detection of such laminin or a fragment thereof, it has been reported, is likely to be used for the diagnosis of various diseases such as hepatic fibrosis/cirrhosis, alcoholic hepatic fibrosis, diabetic complications, kidney diseases, chronic polyarthritis, tumors, and Alzheimer's disease.

Also, for anti-laminin-1 antibody that is an auto-antibody against laminin, it has been reported that anti-laminin antibody can be detected in the serum of monkeys that tend to abort easily, that the addition of serum containing anti-laminin antibody into rat's fetus causes anomalies in the fetus, that immunization of anti-laminin antibody into mice can induce abortion, and the like (Fertil. Steril, 51, 711–718 (1989); Teratology 40, 47–57 (1989); Proc. Natl. Acad. Sci. USA, 92, 6818–6822 (1995); Am. J. Pathol., 110, 346–357 (1983)), and therefore-anti-laminin antibody has been estimated to be one of the factors responsible for abortion.

However, for the significance of determination of anti-laminin antibody in humans, it has only been reported that the assay of auto-antibody against laminin with a molecular weight of 200 kDa that specifically occurs in the urine but not in the serum may be used for the diagnosis of systemic lupus erythematosus (SLE) (Japanese Unexamined Patent Publication (Kokai) No. 8-36966; J. Autoimmun., 8(2), 279–291 (1995)), and no suggestion has been made on whether or not it can be used for the diagnosis of gynecology-related diseases such as habitual abortion, sterility, infertility, and endometriosis.

DISCLOSURE OF THE INVENTION

After intensive and extensive research focusing on laminin as a new marker in gynecology-related diseases, the present inventors have found that anti-laminin-1 antibody, an auto-antibody against laminin-1 (molecular weight: about 900 kDa) in various isoforms, is present specifically in the serum of patients with a gynecology-related disease such as habitual abortion, sterility, infertility, and endometriosis, and the assay of this anti-laminin-1 antibody is useful for the diagnosis of gynecology-related diseases, and thereby have completed the present invention.

Thus, the present invention relates to an assay method for anti-laminin-1 antibody in a sample wherein the sample is allowed to react with laminin-1 or a fragment thereof, and then an assay is carried out to determine whether or not anti-laminin-1 antibody in the sample bound to laminin-1 or a fragment thereof.

The present invention also relates to a kit for use in an assay method for determining the antibody amount of anti-laminin-1 antibody in a sample, said kit comprising laminin-1 or a fragment thereof as component reagents.

Furthermore, the present invention relates to a method of detecting a gynecology-related disease based on the measured value of anti-laminin-1 antibody in the sample determined by the above assay method or by the above kit.

BEST MODE FOR CARRYING OUT THE INVENTION

Figure 1A:
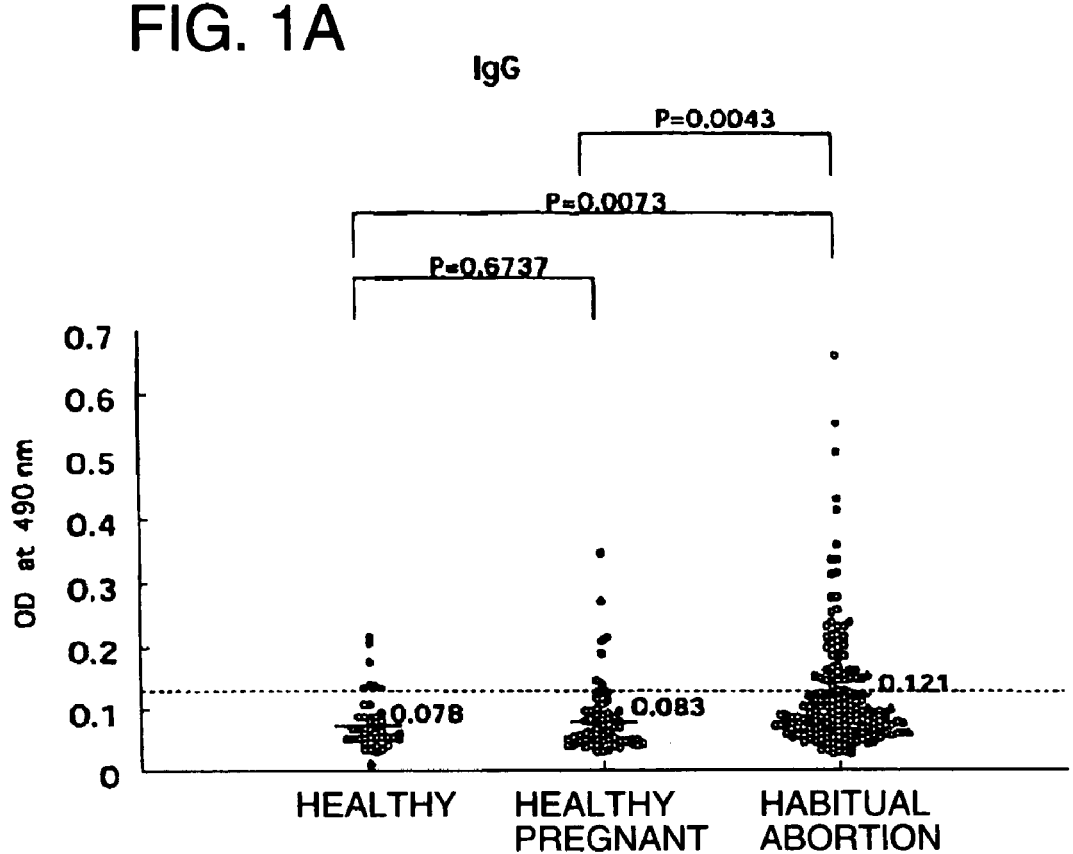
FIG. 1A and FIG. 1B show the result of measurement of anti-laminin-1 antibody (IgG/IgM) in samples taken from healthy women, healthy pregnant women and habitual aborters.

Samples to be assayed are not specifically limited, as long as they are samples suspected of containing anti-laminin-1 antibody. Specific examples of such samples include human blood, serum, plasma etc., and serum and plasma samples are particularly preferred.

The assay of anti-laminin-1 antibody in samples can be carried out by allowing the samples to react with laminin-1, and then determining whether or not anti-laminin-1 antibody in the samples bound to laminin-1.

As laminin-1 to be used, those prepared from cancer cells according to a known method (J. Biol. Chem., 254, 9933–9937 (1979)), or commercially available laminin-1 (Asahi Techno Glass Corporation) can be used.

Also, as long as they do not lose the reactivity with anti-laminin-1 antibody in the samples, they may be fragments obtained by the enzymatic or the chemical treatment of laminin-1, or recombinant fragments etc. produced by DNA recombinant technology using the gene encoding them. As such fragments, there can be mentioned the G domain of laminin-α1 chain (amino acid residues 2111–3060; J. Biol. Chem., 275(38) 29458–29465 (2000)), and the like.

As the form of laminin-1 or a fragment thereof used, compounds in the immobilized form or the labelled form can be used.

The quality of materials for carriers used in the immobilization of laminin-1 or a fragment thereof is not specifically limited, as long as it has a high binding ability with laminin-1 or a fragment thereof, and there can be mentioned, for example, synthetic organic polymer compounds such as polyvinyl chloride, polystyrene, styrene-divinyl benzene copolymers, styrene-maleic anhydride copolymers, nylon, polyvinyl alcohol, polyacrylamide, polyacrylonitrile and polypropylene, polysaccharides such as dextran derivatives (Sephadex etc.), agarose gel (Sepharose, Biogel etc.) and cellulose (paper disc, filter paper etc.), inorganic polymer compounds such as glass, silica gel and silicone, and these may have introduced therein functional groups such as amino groups, aminoalkyl groups, carboxyl groups, acyl groups, and hydroxy groups.

As the shape of carriers, there can be illustrated a plate shape such as microtiter plates and discs, a particulate shape such as beads, a tubular shape such as test tubes and tubings, and further a fibrous shape, a membrane shape etc. and can be selected as appropriate depending on the assay method.

The immobilization of laminin-1 or a fragment thereof may be carried out using known methods such as physical adsorption, ionic binding, covalent bonding and inclusion.

Immobilized reagents thus obtained may be subjected to a blocking treatment using common blocking agents such as BSA, sugar, and skim milk in order to suppress non-specific binding.

Also, when labelled laminin-1 or a fragment thereof are prepared, radioisotopes ($^{32}P$, $^{3}H$, $^{14}C$, $^{125}I$ etc.), enzymes (β-galactosidase, peroxidase, alkaline phosphatase etc.), coenzymes and prosthetic groups (FAD, FMN, ATP, biotin, hem etc.), fluorogenic dyes (fluorescence derivatives, rhodamine derivatives etc.), metal particles (gold, silver, platinum etc.) and the like can be used as labels that can be used.

Labelling of laminin-1 or a fragment thereof can be carried out according to a known method (see, for example, "Zoku-Seikagaku Jikkenkoza 5, Mennekiseikagaku Kenkyuho (Sequel to Biochemistry Experiment Series 5, Immunological Biochemistry Research Method)", Tokyo Kagaku Dojin Co., Ltd. (issued in 1986), pages 102–112) suitable for the labelling agent selected.

The determination of anti-laminin-1 antibody in a sample using such an immobilized and/or labelled compound may be carried out according to a method commonly used as an method for antibodies such as an auto-antibody in a sample, and for example a specific assay procedure for anti-laminin-1 antibody in a sample using immobilized laminin-1 or a fragment thereof is as described below.

A Method using Immobilized Laminin-1

(a) samples suspected of containing anti-laminin-1 antibody are incubated with a solid-phase carrier having laminin-i or a fragment thereof immobilized thereon, (b) said solid-phase carrier is washed to remove an excess of samples, (c) said solid-phase carrier is incubated with a labelled anti-human immunoglobulin antibody, and (d) the solid-phase and the liquid-phase are separated (BF separation), and the amount of label in either of them is determined in order to calculate the antibody amount of anti-laminin-1 antibody in the samples.

A specific assay procedure for the determination of anti-laminin-1 antibody in a sample using labelled laminin-1 or a fragment thereof is as described below.

A Method using Labelled Laminin-1

(a) samples suspected of containing anti-laminin-1 antibody are incubated with the labelled laminin-1 or a fragment thereof, (b) labelled laminin-1 or a fragment thereof bound to anti-laminin-1 antibody and unbound labelled laminin-1 or a fragment thereof are separated, and (c) the amount of label in either of the phases is determined in order to calculate the antibody amount of anti-laminin-1 antibody in the samples.

Also, a kit for determining anti-laminin-1 antibody need only to include laminin-1 or a fragment thereof as component reagents of the kit, and for other component reagents those reagents required, as appropriate, depending on the assay method adopted by the kit need only to be attached. For example, as a kit for determining anti-laminin-1 antibody using immobilized laminin-1 or a fragment thereof, one described below may be illustrated:

1) immobilized laminin-1 or a fragment thereof
2) labelled anti-human immunoglobulin antibody.

Also, as a kit for determining anti-laminin-1 antibody using labelled laminin-1 or a fragment thereof, one described below may be illustrated:

1) labelled laminin-1 or a fragment thereof
2) an agent for BF separation [DCC (dextran-coated activated charcoal), polyethylene glycol, ammonium sulfate etcl].

Furthermore, to the above kit may be attached, as appropriate, reagents (a sample dilution solution, a washing solution, an enzyme substrate solution, a reaction stopping solution, a standard antibody solution etc.) required for the assay method adopted or the type of label.

Using such a kit, anti-laminin-1 antibody in a sample may be determined in the above-mentioned method, and the result is compared with the measured value for healthy women, and when the result is higher than the level of the healthy women, the possibility of a gynecology-related disease such as habitual abortion, sterility, infertility, and endometriosis should be considered to be high, and preferably close examination should be carried out.

EXAMPLES

The present invention will now be specifically explained with reference to Examples. It should be noted, however, that the present invention is not limited by them in any way.

Example 1

(1) Samples

Blood was taken as a sample from 207 women with a history of abortion (habitual abortion) (mean age: 31.0±3.8 years old, mean number of abortion: 2.7±1.1), 100 healthy pregnant women (mean age: 30.7±4.5 years old), and 40 healthy non-pregnant women (mean age: 29.6±5.1 years old). However, of 207 women with a history of abortion, 30 having an allergy disease were excluded from the measurement.

(2) Assay

1) Assay for β2-GPI-dependent Anti-cardiolipin Antibody

The ELISA of β2-dependent anti-cardiolipin antibody was carried out by the method of Matsuura (J. Immunol. 148, 3885–3891 (1992)) with minor modifications. Thus, cardiolipin (2.5 μg/50 μl/well) was coated onto a polystyrene microtiter plate (Immulon-1; Dynex Technologies Inc.), and after blocking with 1% BSA, human β2-GPI (1.0 μg/50 μl) and 100-fold diluted serum samples (50 μl) were added to each well, which were stirred well, and then incubated at room temperature for 30 minutes.

After incubation, a tetramethylbenzidine solution containing hydrogen peroxide is added and allowed to react. Then 2N sulfuric acid is added to stop the reaction, absorbance at 450 nm is measured, and antibody titer (units/ml) of anti-cardiolipin antibody is calculated from the standard curve.

2) Assay for Lupus Anticoagulants (LA)

Using cerebral cephalin as a phospholipid to determine the time (aPPT) to partially activate thromboplastin, non-pregnant control serum (50 μl), standard plasma (50 μl), and diluted cerebral cephalin (100 μl) are mixed, incubated at 37° C. for exactly 3 minutes, 100 μl of 25 mM $CaCl_2$ is added, and coagulation time is measured.

If the elongated coagulation time (mean+3SD longer than 7.37 seconds) does not return to the original time when the standard plasma and a sample plasma were mixed at 1:1, LA is considered to be positive.

3) Assay for Anti-Nuclear Antibody (ANA) and Anti-DNA Antibody

According to a known method (Am. J. Med., 89, 129–133 (1990)), ANA was measured by an indirect immunofluorescent method using HepG2 cell slides, and anti-DNA antibody was measured using a commercially available kit.

4) Assay for Anti-Laminin-1 Antibody

Laminin-1 was prepared by a known method (J. Biol. Chem., 254, 9933–9937 (1979)).

A microtiter plate (Immulon-IB: Dynex Technologies Inc.) is coated (50 μl/well) with laminin-1 (10 μg/ml), incubated overnight at 4° C., and after it was blocked with 10% bovine fetal serum, 200-fold diluted serum samples (100 μl/well) are added, and incubated at room temperature for 1 hour.

After incubation, an anti-human immunoglobulin (IgG/IgM) antibody labelled with horseradish peroxidase (HRP) is added, and incubated at room temperature for 1 hour. After an o-phenylenediamine solution containing hydrogen peroxide is added and allowed to react. Then 2N sulfuric acid is added to stop the reaction, and absorbance at 490 nm is measured. When the measured value is higher than the mean+SD of anti-laminin-1 antibody in the plasma of healthy non-pregnant women, anti-laminin-1 antibody is considered to be positive.

(3) Results

Figure 1B:
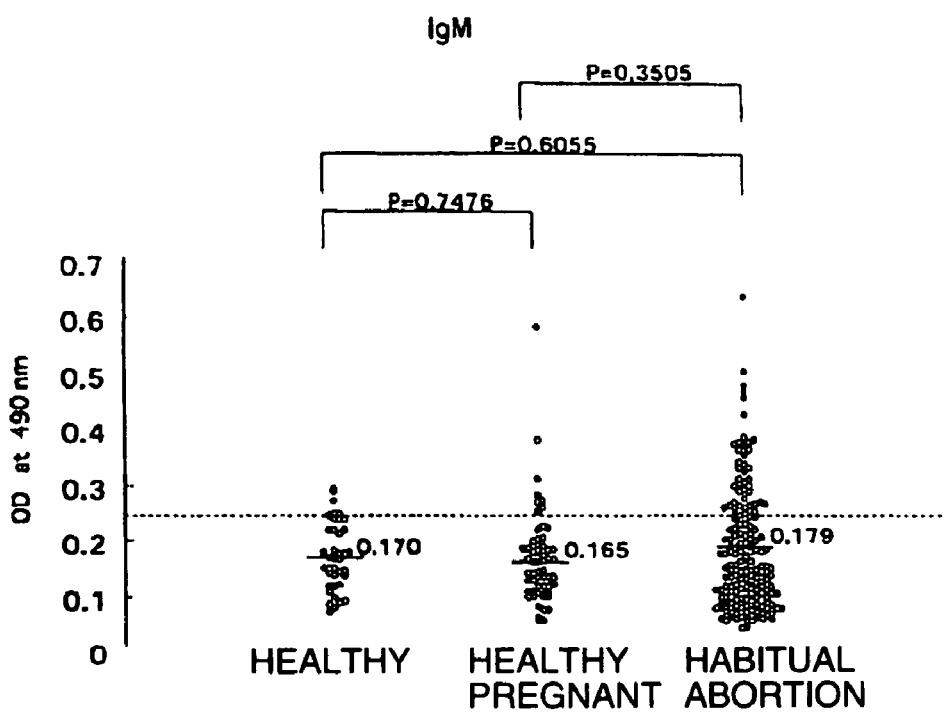

As a result of assaying the above samples, levels of anti-laminin-1 antibody (IgG) in samples taken from women with habitual abortion were significantly higher than those of anti-laminin-1 antibody (IgG) for healthy pregnant women and healthy women (P=0.0043, P=0.0073) (see FIG. 1).

Furthermore, anti-laminin-1 antibody (IgG) was positive in 55 samples (31.1%) out of 177 samples of habitual abortion, and negative in 122 samples (68.9%). Also, anti-laminin-1 antibody (IgM) was positive in 49 samples (27.7%) and negative in 128 samples (72.3%).

As a result of analyzing the probability of normal childbirth, as shown in Table 1, the probability of normal childbirth in anti-laminin-1 antibody (IgG)-positive habitual abortions was found to be significantly lower than that of normal childbirth in anti-laminin-1 antibody (IgG)-negative habitual abortions.

Also, between the anti-laminin-1 antibody-positive habitual abortions and the anti-laminin-1 antibody-negative habitual abortions, there were no significant differences in the age of pregnant women, the number of abortions, etc.

Table 1: Association of Anti-laminin-1 Antibody and the Number of Abortions and Progress of Pregnancy

TABLE 1

Association of anti-laminin-1 antibody and the number of abortions and progress of pregnancy

| | Anti-laminin-1 antibody (IgG) | | |
|---|---|---|---|
| | Positive (n = 38) | Negative (n = 85) | Fisher's exact test (p value) |
| Age | 30.0 ± 3.9 | 30.0 ± 3.3 | No significant difference |
| No. of past abortions | 2.8 ± 1.5 | 2.8 ± 1.3 | No significant difference |
| Progress of pregnancy Normal birth | 19 | 50 | |
| Probability (%) | 50.0 | 69.4 | 0.032 |

As a result of analyzing the correlation between anti-laminin-1 antibody and other auto-antibodies in habitual abortion, as shown in Table 2, no correlation was found between anti-laminin-1 antibody and other auto-antibodies. The prevalence of auto-antibodies in 55 samples of anti-laminin-1 antibody (IgG)-positive habitual abortion was 1.8% (1/55) for β2-GPI-dependent anti-cardiolipin antibody (aCL), 20.0% (11/55) for LA, 14.5% (8/55) for anti-DNA antibody, and 21.8% (12/55) for anti-nuclear antibody (ANA).

TABLE 2

Correlation of anti-laminin-1 antibody and other auto-antibodies in habitual abortion

| | Anti-laminin-1 antibody (IgG) | |
|---|---|---|
| | Positive | Negative |
| aCL % | 31.1 | 68.9 |
| positive | 1 | |
| negative | 54 | 3 |
| Fisher's exact test | No significant difference | 119 |
| P value | | |
| LA % | 31.1 | 68.9 |
| positive | 11 | |
| negative | 44 | 16 |
| P value | No significant difference | 106 |
| Anti-DNA antibody % | 31.1 | 68.9 |
| positive | 8 | |
| negative | 47 | 18 |
| P value | No significant difference | 10 |
| ANA % | 31.1 | 68.9 |
| positive | 12 | |
| negative | 43 | 17 |
| P value | No significant difference | 105 |

Example 2

In an investigation of the association of infertility and anti-laminin-1 antibody carried out according to the method described in Example 1, anti-laminin-1 antibody (IgG) was positive in 12 samples (24.0%), negative in 38 samples (76.0%) of 50 samples of infertile patients who underwent in vitro fertilization (IVF), exhibiting a significantly high prevalence as compared to healthy women (P=0.0088).

Also, the positivity of anti-laminin-1 antibody (IgG) in infertile patients (IVF) with complicated endometriosis, as shown in Table 3, exhibited a very high value of 75% (6 of 8 were positive).

TABLE 3

Positivity of anti-laminin-1 antibody in infertile patients with complicated endometriosis

| Anti-laminin-1 antibody (IgG) | % | Endometriosis Positive | Endometriosis Negative | Fisher's exact test (p value) |
|---|---|---|---|---|
| Positive | 75.0 | 6 | 6 | 0.00127 |
| Negative | 25.0 | 2 | 36 | |

Example 3

(1) Samples

Plasma samples were collected from 53 infertile patents who underwent laparoscopy or laparotomy (mean age: 33.4±4.7 years; range: 26–45 years), from 50 infertile patients who underwent in vitro fertilization and embryo transfer (IVF-ET) (mean age: 34.1±4.4 years; range: 23–45 years; mean number of IVF: 2.8±2.6), and from 39 healthy non-pregnant women (mean age: 29.6±5.1 years; range: 22–41 years). In IVF patients, plasma samples were taken on the day before transvaginal oocyte pick-up. The clinical profiles of these infertile patients are shown in Table 4. The infertile patients included unexplained uterine and hormone abnormality. Of the 50 IVF patients, 8 had endometriosis. The 53 infertile patients who underwent laparoscopy or laparotomy were divided into two groups, with and without endometriosis, based on the laparoscopic or laparotomic findings. The severity of endometriosis was classified according the revised classification of the American Fertility Society (AFS). Thus, of the 34 infertile patients with endometriosis, 7 had stage I (minimal), 6 had stage II (mild), 13 had stage III (moderate), and 8 had stage IV (severe) disease.

1) Assay for Anti-laminin-1 Antibody

In a method substantially similar to the one described in (2) 4) of Example 1, anti-laminin-1 antibody in plasma samples was determined. When the measured levels were higher than mean+SD of anti-laminin-1 antibody in plasma samples from healthy non-pregnant women, anti-laminin-1 antibody was considered positive.

2) Measurement of Cancer Antigen 125 (CA-125)

CA-125 was measured in the plasma samples using a commercially available immunoradiometric assay kit (CA-125 II IRMA kit; Centcore, Inc., Malvern, Pa.) (Cancer Research 1984; 44:1048–53). Results were obtained from the standard curve. A value of 20 U/ml was applied as a cut-off value. Incidentally, CA-125 has also been used as a marker for endometriosis.

3) Assay for Anti-laminin-1 Antibody using the G Domain of Laminin-α1 Chain

Using the Hitrap heparin-affinity column and the FPLC system, the recombinant G domain of laminin-α1 chain was purified from the culture of Chinese Hamster oocytes transformed with a plasmid encoding the G domain (amino acid residues #2222–3060) of laminin-α1 chain (J. Biol. Chem., 2000; 275:29458–65). The recombinant G domain was coated onto a polystyrene plate (Immulon 1B) (1 μg/50 μl/well), incubated overnight at 4° C., and then blocked. 25-fold diluted samples (100 μl/well) were added to wells, and were incubated at room temperature for 1 hour. Then, in a method similar to the one described in (2) 4) of Example 1, anti-laminin-1 antibody bound to the recombinant G domain of laminin-α1 chain was determined.

(3) Results

1) Association of Anti-laminin-1 Antibody and the Causes of Infertility

For samples from 103 infertile patients including 50 IVF patients and from 39 healthy women, anti-laminin-1 antibody was determined to analyze the association of the cause of infertility and anti-laminin-1 antibody levels. The result obtained is shown in Table 4. As can be seen from Table 4, there was a significant correlation between the anti-laminin-1 antibody-positive patients and endometriosis. Of 32 patients positive for anti-laminin-1 antibody, 21 (66%) had endometriosis, and of 71 patients negative for anti-laminin-1 antibody, 21 (30%) (p=0.00063) had endometriosis. There was no significant correlation between other causes of infertility and anti-laminin-1 antibody-positive patients.

TABLE 4

Anti-laminin-1 antibody and clinical profiles

|  |  | Anti-laminin-1 antibody (IgG) | | |
|---|---|---|---|---|
| Clinical profiles |  | Positive (n = 32) | Negative (n = 71) | Fisher's exact test (p value) |
| Mean age (±SD) | 33.8 ± 4.6 | 33.5 ± 4.5 | 33.9 ± 4.6 | No significant difference |
| Diagnosis of infertility (cause of infertility) |  |  |  |  |
| Fallopian tube | 24/103 (23%) | 6/32 (19%) | 18/71 (25%) | No significant difference |
| Male | 24/103 (23%) | 4/32 (13%) | 20/71 (28%) | No significant difference |
| Endometriosis | 42/103 (41%) | 21/32 (66%) | 21/71 (30%) | 0.00063 |
| Fallopian tube and male | 2/103 (1.9%) | 0/32 (0%) | 2/71 (30%) | No significant difference |
| Fallopian tube and endometriosis | 12/103 (12%) | 5/32 (16%) | 7/71 (10%) | No significant difference |
| Male and endometriosis | 4/103 (3.9%) | 2/32 (0.3%) | 2/71 (2.8%) | No significant difference |
| Unknown | 35/103 (34%) | 9/32 (28%) | 26/71 (37%) | No significant difference |

Figure 2:
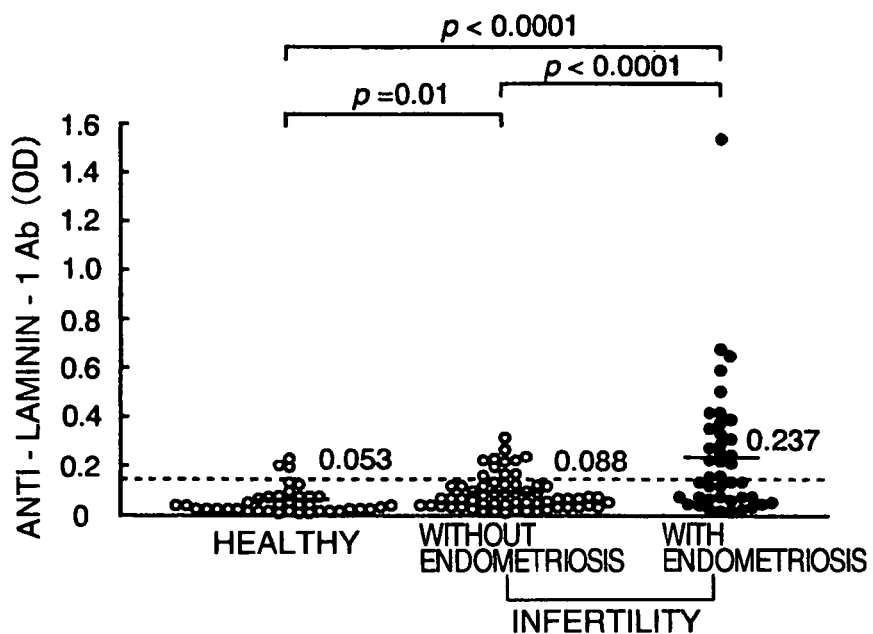
FIG. 2 shows the result of measurement of anti-laminin-1 antibody (IgG) in samples taken from healthy non-pregnant women, infertile patients with endometriosis and infertile patients without endometriosis.

FIG. 2 shows the assay result of anti-laminin-1 antibody (IgG) in the samples collected from healthy non-pregnant women, infertile patients with endometriosis and infertile patients without endometriosis. As can be seen from FIG. 2, anti-laminin-1 antibody levels in infertile patients (n=103) were significantly higher than those in healthy non-pregnant women (n=39) (p=0.0029). Of 103 infertile patients, 32 (31%) were positive for anti-laminin-1 antibody. Anti-laminin-1 antibody levels in infertile patients with endometriosis were significantly higher than those in healthy non-pregnant women and infertile patients without endometriosis (p<0.0001).

Figure 3:
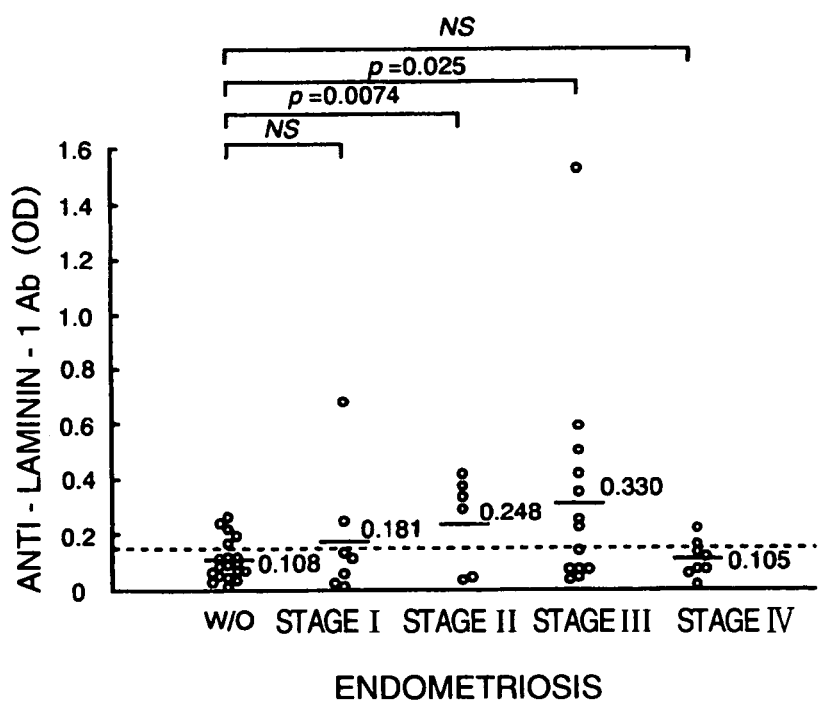
FIG. 3 shows the relationship of severity of endometriosis and levels of anti-laminin-1 antibody.

For the 53 infertile patients who underwent laparoscopy or laparotomy, relationship between the severity of endometriosis and anti-laminin-1 antibody levels was examined. The result is shown in FIG. 3. As can been seen from FIG. 3, anti-laminin-1 antibody levels in infertile patients with stage II or stage III endometriosis were fairly higher than those in stage I or stage IV patients. Levels in stage II or stage III patients were significantly higher than infertile patients without endometriosis (p=0.0074 and p=0.0025, respectively). Levels in stage I and IV patients were not significantly different from those in patients without endometriosis. Four (67%) out of 6 infertile patients at stage II and 7 (54%) out of 13 infertile patients at stage III were positive for anti-laminin-1 antibody.

2) Relationship Between Endometriosis and Anti-laminin-1 Antibody and CA-125 in IVF Patients Relationship between endometriosis and anti-laminin-1 antibody and CA-125 in IVF patients is shown in Table 5. As can be seen from Table 5, the prevalence of positive anti-laminin-1 antibody in IVF patients was significantly higher in patients with endometriosis than those without endometriosis (6 (14%) of 42 patients without endometriosis were positive whereas 6 (75%) of 8 patients with endometriosis were positive; p=0.003). There was no significant relationship between patients with endometriosis and the presence of CA-125 (11 (26%) of 42 patients without endometriosis were positive for CA-125, whereas 4 (50%) of 8 patients with endometriosis were positive for CA-125; p=0.18).

TABLE 5

Relationship between endometriosis and anti-laminin-1 antibody and CA-125 in IVF patients

| Serological parameters | Endometriosis | | Fisher's exact test (p value) |
|---|---|---|---|
|  | Positive | Negative |  |
| Anti-laminin-1 antibody (IgG) |  |  |  |
| Positive | 6 | 6 | 0.0013 |
| Negative | 2 | 36 |  |
| CA-125 |  |  |  |
| Positive | 4 | 11 | No significant difference (0.18) |
| Negative | 4 | 31 |  |

Figure 4:
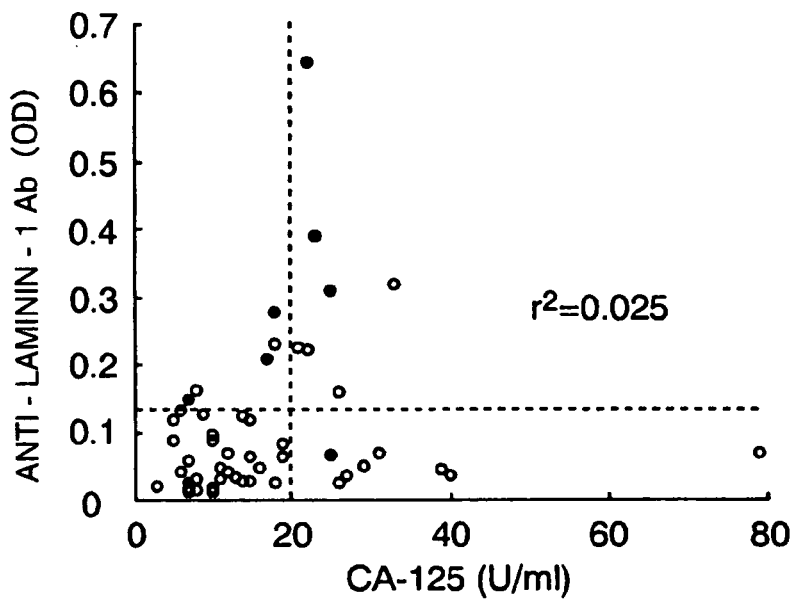
FIG. 4 shows the correlation of levels of anti-laminin-1 antibody and CA-125 values.

Table 6 shows the relationship between anti-laminin-1 antibody and CA-125 in IVF patients. As can be seen from Table 6, there was a significant correlation between positive anti-laminin-1 antibody and positive CA-125 in IVF patients (p=0.020). As is shown in FIG. 4, however, there was no correlation between anti-laminin-1 antibody levels and CA-125 values ($r^2$=0.025).

TABLE 6

Relationship between anti-laminin-1 antibody and CA-125 in IVF patients

|  | Anti-laminin-1 antibody (IgG) | | Fisher's exact test (p value) |
|---|---|---|---|
| CA-125 | Positive | Negative |  |
| Positive | 7 | 8 | 0.020 |
| Negative | 5 | 30 |  |

Figure 5:
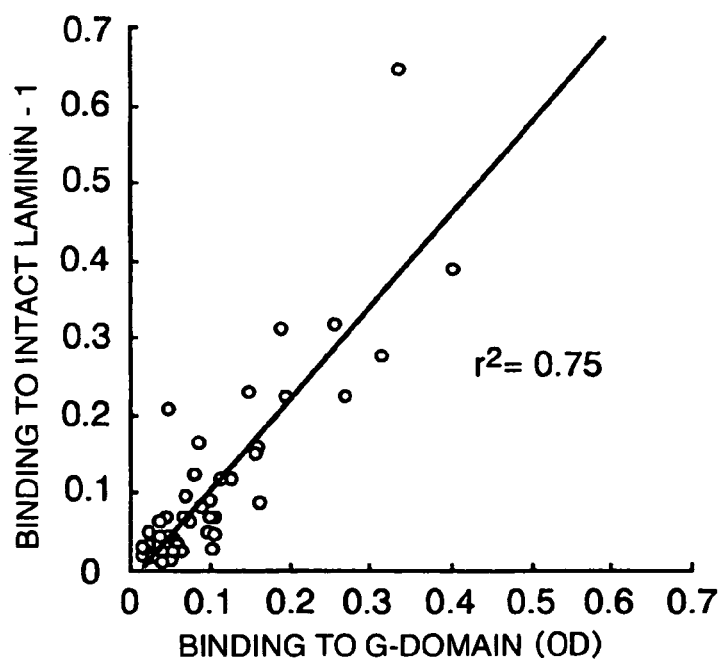
FIG. 5 shows the cross-reactivity of anti-laminin-1 antibody in IVF patients to laminin-1 and to the G domain of laminin-α1 chain.

3) Cross-Reactivity of Anti-Laminin-1 Antibody to Laminin-1 and the G Domain of Laminin-α1 Chain in IVF Patients Samples collected from 50 IFV patients were used to examine whether anti-laminin-1 antibody recognize the G domain of laminin-α1 chain. The result obtained is shown in FIG. 5. As can be seen from FIG. 5, anti-laminin-1 antibody in samples from IVF patients cross-reacted with the G domain. Furthermore, there was a correlation between the immuno-reactivity of anti-laminin-l antibody and the intact laminin-1 molecule, and the immuno-reactivity of anti-laminin-1 antibody and the G domain.

INDUSTRIAL APPLICABILITY

Since an auto-antibody (anti-laminin-1 antibody) against laminin-1 among various laminin isoforms is present specifically in the plasma or serum of patients with gynecology-related diseases such as habitual abortion, sterility, infertility, and endometriosis, and this auto-antibody has no correlation with other auto-antibodies (for example, anti-phospholipid antibody, anti-DNA antibody, anti-nuclear antibody etc.) found in autoimmune diseases, it was found by the present inventors, for the first time, that this antibody is clinically useful as a novel marker for gynecology-related diseases in humans.

The invention of claimed is:

1. A method for diagnosing endometriosis in an infertile female suspected of having endometriosis, which comprises the steps of:

(a) reacting a test sample from the infertile female suspected of having endometriosis with laminin-1 or a fragment thereof to thereby bind anti-laminin-1 antibody in the test sample to the laminin-1 or fragment;

(b) determining an amount of the anti-laminin-1 antibody in the test sample which is bound to the laminin-1 or fragment;

(c) comparing the amount of bound anti-laminin-1 antibody in the test sample with the amount of bound anti-laminin-1 antibody in a control sample from a healthy female, wherein a higher amount of bound anti-laminin-1 antibody in the test sample is indicative of a diagnosis of endometriosis.

2. The method according to claim 1, wherein the laminin-1 or fragment thereof in step (a) is immobilized on a solid-phase, and the amount of anti-laminin-1 antibody in the test sample in step (b) is determined by reacting the laminin-1 or fragment after step (a) with a labeled anti-human immunoglobulin antibody followed by measuring the amount of the label.

3. The method according to claim 1, wherein the laminin-1 or fragment thereof in step (a) is labeled, and the amount of anti-laminin-1 antibody in the test sample is determined by measuring the amount of the label.

4. The method according to claim 1, wherein the sample is blood, plasma or serum.

* * * * *